(12) United States Patent
Davalian

(10) Patent No.: US 7,828,996 B1
(45) Date of Patent: Nov. 9, 2010

(54) METHOD FOR THE MANUFACTURE OF STABLE, NANO-SIZED PARTICLES

(75) Inventor: Dariush Davalian, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 12/413,478

(22) Filed: Mar. 27, 2009

(51) Int. Cl.
*B01F 11/00* (2006.01)

(52) U.S. Cl. .............................. 264/9; 264/5; 264/405; 425/6

(58) Field of Classification Search ............... 264/9, 264/5, 405, 109; 425/6
See application file for complete search history.

(56) References Cited

U.S. PATENT DOCUMENTS

| | | | |
|---|---|---|---|
| 3,737,337 A | 6/1973 | Schnoring et al. | |
| 4,162,282 A * | 7/1979 | Fulwyler et al. | ............... 264/9 |
| 4,826,689 A | 5/1989 | Violanto | |
| 5,145,684 A | 9/1992 | Liversidge et al. | |
| 5,298,262 A | 3/1994 | Na et al. | |
| 5,302,401 A | 4/1994 | Liversidge et al. | |
| 5,336,507 A | 8/1994 | Na et al. | |
| 5,340,564 A | 8/1994 | Illig et al. | |
| 5,346,702 A | 9/1994 | Na et al. | |
| 5,352,459 A | 10/1994 | Hollister et al. | |
| 5,354,560 A | 10/1994 | Lovrecich | |
| 5,384,124 A | 1/1995 | Courteille et al. | |
| 5,429,824 A | 7/1995 | June | |
| 5,503,723 A | 4/1996 | Ruddy et al. | |
| 5,510,118 A | 4/1996 | Bosch et al. | |
| 5,518,187 A | 5/1996 | Bruno et al. | |
| 5,518,738 A | 5/1996 | Eickhoff et al. | |
| 5,534,270 A | 7/1996 | De Castro | |
| 5,536,508 A | 7/1996 | Canal et al. | |
| 5,552,160 A | 9/1996 | Liversidge et al. | |
| 5,560,931 A | 10/1996 | Eickhoff et al. | |
| 5,560,932 A | 10/1996 | Bagchi et al. | |
| 5,565,188 A | 10/1996 | Wong et al. | |
| 5,569,448 A | 10/1996 | Wong et al. | |
| 5,571,536 A | 11/1996 | Eickhoff et al. | |
| 5,573,783 A | 11/1996 | Desieno et al. | |
| 5,580,579 A | 12/1996 | Ruddy et al. | |
| 5,585,108 A | 12/1996 | Ruddy et al. | |
| 5,587,143 A | 12/1996 | Wong | |
| 5,591,456 A | 1/1997 | Franson et al. | |
| 5,622,938 A | 4/1997 | Wong | |

(Continued)

FOREIGN PATENT DOCUMENTS

WO 93/25190 12/1993

(Continued)

OTHER PUBLICATIONS

U.S. Appl. No. 12/165,173, filed Jun. 30, 2008, Ngo et al.

(Continued)

*Primary Examiner*—Khanh Nguyen
*Assistant Examiner*—Saeed M Huda
(74) *Attorney, Agent, or Firm*—Squire, Sanders & Dempsey L.L.P.

(57) ABSTRACT

The current invention relates to methods of making nanoparticles of a material with a narrow polydispersity. The particle materials are active agents, organic compounds, polymers, and combinations thereof.

21 Claims, 2 Drawing Sheets

U.S. PATENT DOCUMENTS

| | | | |
|---|---|---|---|
| 5,662,883 | A | 9/1997 | Bagchi et al. |
| 5,665,331 | A | 9/1997 | Bagchi et al. |
| 5,718,919 | A | 2/1998 | Ruddy et al. |
| 5,747,001 | A | 5/1998 | Wiedmann et al. |
| 5,916,596 | A | 6/1999 | Desai et al. |
| 6,440,493 | B1 * | 8/2002 | Gibson et al. ............ 427/213.3 |
| 6,506,411 | B2 | 1/2003 | Hunter et al. |
| 6,623,761 | B2 | 9/2003 | Hassan |
| 6,998,051 | B2 | 2/2006 | Chattopadhyay et al. |
| 2004/0170654 | A1 | 9/2004 | Pinkerton |

FOREIGN PATENT DOCUMENTS

| | | |
|---|---|---|
| WO | 96/24336 | 8/1996 |
| WO | 97/14407 | 4/1997 |
| WO | 98/35666 | 8/1998 |
| WO | 99/65469 | 12/1999 |
| WO | 00/18374 | 4/2000 |
| WO | 00/27369 | 5/2000 |
| WO | 00/30615 | 6/2000 |
| WO | 03/002094 | 1/2003 |
| WO | 03/002103 | 1/2003 |
| WO | 2008/054523 | 5/2008 |

OTHER PUBLICATIONS

"*90Plus Particle Size Analyzer*" Brookhaven Instruments Corp. downloaded from www.bic.com/90Plus.html., Mar. 4, 2008, 6 pgs.

"*Available Particle Characterization Technologies*", downloaded from www.malvern.com/LabEng/support/technologies.htm., Mar. 5, 2008, 3 pgs.

"*Laser Light Scattering*", downloaded from www.ap-lab.com/light_scattering.htm, Mar. 5, 2008, 8 pgs.

"Microemulsion characterization using dynamic light scattering", Zetasizer Nano application note, downloaded from www.malvern.co.uk, 3 pgs. no date.

"*Pigment Milling and Monitoring Particle Size Using Dynamic Light Scattering Techniques from Malvern Instruments*", downloaded from www.azom.com/details.asp?ArticleID=2724, Apr. 10, 2008, 5 pgs.

"Sonication 101", downloaded from www.opsdiagnostics.com/notes/ranpri/rpsonication101.htm, Dec. 12, 2008, 1 pg.

"*Taking the "suspense" out of Nanosuspension Specifications*", downloaded from www.pharmtech.findpharma.com/pharmtech/content/printContentPopup.jsp, Apr. 9, 2008, 3 pgs.

"*Toner size and shape characterization using FPIA-2100*", FPIA-2100 application note, downloaded from www.malvern.co.uk, 5 pgs. no date.

"Ultrasonics", from Wikipedia, the free encyclopedia, downloaded: http://en.wikipedia.org/wiki/Ultrasonics, Dec. 22, 2008, 2 pgs.

"*When Particle Size is Important*", Brookhaven Instruments corp. downloaded from www.bic.com/Particle_sizers_overview.html, Mar. 5, 2008, 7 pgs.

Banert et al., "Operating parameters of a continuous sono-chemical precipitation reactor", Fifth World congress on Particle Technology 10 pgs. (2006).

Berkland et al., "*Controlling surface namo-structure using flow-limited field-injection electrostatic spraying (FFESS) of poly(D, L-lactide-co-glycolide)*", Biomaterials 25, pp. 5649-5658 (2004).

Berkland et al., "Fabrication of PLG microspheres with precisely controlled and monodisperse size distributions", J. of Controlled Release 73, pp. 59-74 (2001).

Berkland et al., "*Precise control of PLG microsphere size provides enhanced control of drug release rate*", J. of Controlled Release 82, pp. 137-147 (2002).

Berkland et al., "*Precission Polymer Microparticles for Controlled-Release Drug Delivery*", Am. Chem. Soc. pp. 197-213 (2004).

Bin Choy et al., "*Uniform Biodegradable Hydrogel Microspheres Fabricated by a Surfactant—Free Electric-Field-Assisted Method*", Macromol. Biosci. vol. 7, pp. 423-428 (2007).

Costa et al., "Effect of uniform sized polymeric microspheres prepared by membrane emulsification technique on controlled release of anthracycline anti-cancer drugs", Desalination vol. 200, issues 1-3, pp. 498-500 (2006).

Dubey et al., "*Factorial Effect of Process Parameters on Pharmaceutical Characteristics & Stability Study of PLGA Microspheres Containing Water-Soluble Drug*", downloaded from www.drugdeliverytech.com/cgi-bin/articles.cgi?idArticle=229, Apr. 9, 2008, 13 pgs.

Finsy et al., "*Particle Sizing by Photon Correlation Spectroscopy. Part II: Average values*", Particle and particle Systems Characterization vol. 8, issue 1-4, pp. 187-193, Abstract 1 pg. (2004).

Han et al., "Stability and size dependence of protein microspheres prepared by ultrasonication", J. Mat. Chem. 18; pp. 5162-5166 (2008) Abstract.

Hanus et al., "*Conversion of intensity-averaged photon correlation spectroscopy measurements to number-averaged particle size distributions. 1. Theoretical development*", Langmuir vol. 15, No. 9, Abstract 1 pg. (1999).

Hua Ai et al., "*Biomedical applications of electrostatic layer-by-layer nano-assembly of polymers, enzymes, and nanoparticles*", Cell Biochem. and Biophysics, vol. 39, No. 1, Abstract 1 pg. (2003).

Jaroš et al., "The Measuring of Ultrasound Probes", FRVŠ project No. 1657, downloaded from www.feec.vutbr.cz/EEICT/2004/sbornik/03-Doktorskeprojekty/01-Elektronics/13Jaros, 5 pgs.

Kim et al., "*Drug Delivery, Contolled-release*" Office of Technology Management Univ. of Ill., 2 pgs. (2005-2006).

Kippax, "*Measuring particle size using modern laser diffraction techniques*", downloaded from www.analytica-world.com/articles/e/, Mar. 5, 2008, 4 pgs.

Kosvintsev et al., "*Liquid-Liquid Membrane Dispersion in a Stirred Cell with and without Controlled Shear*", Ind. Eng. Chem. Res. 44, pp. 9323-9330 Abstract only, 1 pg. (2005).

Marko et al., "Nonlinear modeling of interactions between ultrasound propagation and cavitation bubbles", OSA/DAGA vol. 92, No. 1, pp. 165-167 (2006) Abstract.

Micropore Technologies *emulsions-particles-filtration*, Abstract, 1 pg. downloaded from www.micropore.co.UK, Mar. 19, 2008.

Nakashima et al., "*Particle control of emulsion by membrane emulsification and its applications*", Advanced Drug Del. Rev. 45 pp. 47-56 (2000).

Nomura et al., "Analysis of an ultrasonic field attenuated by oscillating cavitation bubbles", Acoust. Sci. & Tech. 22, pp. 283-291 (2001).

Servant et al., "Numerical simulation of cavitation bubble dynamics induced by ultrasound waves in a high frequency reactor", Ultrasonics Sonochemistry vol. 7, issue 4, pp. 217-227 (2000) Abstract.

Sjöström et al., "The Formation of Submicron Organic Particles by Precipitation in an Emulsion", Dispersion Science and Techn. 15, pp. 89-117 (1994).

Son et al., "Analysis of the Ultrasonic Cavitation Energy in a Pilot-Scale Sonoreactor", Jpn. J. Appl. Phys. 47, pp. 4119-4122 (2008) Abstract.

Tejinder et al., "Control of crystal size and distribution of zeolite A", Ind. and Engineering Chem. Research vol. 40, No. 4, pp. 1133-1139 (2001) Abstract.

The knowledge database about lactose, Particle Size Distribution D10, D50 and D90, downloaded from www.lactose.com/particle_size/d10_d50_d90.html, Apr. 9, 2008, 2 pgs.

Thorsten et al., "Vibrating nozzle processing in industrial microencapsulation", 15th International Syposium on Microcapsulation, Italy, pp. 25-26, Sep. (2005).

Wu et al., "Effect of Ultrasonication on Droplet Size in Biodiesel Mixtures", J. of the Am. Oil. Chemists Society vol. 84, No. 9, pp. 877-884 (2007) Abstract.

Baba et al., "A New Method for Delivering a Hydrophobic Drug for Photodynamic Therapy Using Pure Nanocrystal Form of the Drug", Mol. Pharm. 4, (2), pp. 289-297 (2007).

Liversidge et al., "Particle size reduction for improvement of oral bioavailability of hydrophobic drugs: I. Absolute oral bioavailability of nanocrystalline danazol in beagle dogs", Int. J. Of Pharm. 125, pp. 91-97 (1995).

Takahashi et al., "Preparation of a novel PEG-clay hybrid as a DDS material:Dispersion stability and sustained release profiles", J. of Controlled Release 107, pp. 408-416(2005).

Nagasaki "Design of porous inorganic nanparticles hybridized with acetal-PEG-b-polyamine block copolymers for high performance drug carrier", Kobunshi Ronbunshu vol. 65, No. 6, pp. 405-415, English Abstract (2008).

* cited by examiner

METHOD FOR THE MANUFACTURE OF STABLE, NANO-SIZED PARTICLES

FIELD

This invention relates to the fields of organic chemistry, pharmaceutical sciences, material science and chemical engineering.

BACKGROUND

Stable nano-size particles of active agents ar useful in the field of pharmaceutical sciences. Smaller particles have a larger surface area and thus are more quickly and completely dissolved, and thus more likely to be orally absorbed. For applications such as coating on implantable medical devices, stable, smaller size active agent particles may reduce the risk of embolism.

Provided herein are simple, economical methods for the production of active agent nanoparticles having a narrow particle size distribution.

SUMMARY

Thus, an aspect of this invention is a method for forming particles of a material by: adding an organic solution comprising a material and an organic solvent to an aqueous solution comprising an emulsifier in about 3 minutes to about 60 minutes wherein the ratio (volume:volume) of organic solution to aqueous solution is about 1:3 to about 1:500; and sonicating the aqueous solution during the addition of the organic solution; wherein the material has an aqueous solubility of 50 mg/ml or less, and the organic solvent has an aqueous solubility of 50 mg/ml or less; wherein the sonication apparatus is at least partially submersed in the aqueous solution but does not touch any part of the apparatus used in the addition of the organic solution to the aqueous solution; and wherein the point of addition of the organic solution to the aqueous solution is within the wave funnel produced by the sonication and within a selected distance from the wave source depending on the desired particle size.

In an aspect of this invention, the sonication apparatus comprises a sonicator probe that is at least partially submersed in the aqueous solution.

In an aspect of the invention, the selected distance is not more than two times the probe diameter.

In an aspect of this invention, the selected distance is not more than one times the probe diameter.

In an aspect of this invention, the selected distance is not more than 80% of the probe diameter.

In an aspect of this invention, the selected distance is not more than 20% of the probe diameter.

In an aspect of this invention, the material has an aqueous solubility of about 25 mg/ml or less.

In an aspect of this invention, the material has an aqueous solubility of about 10 mg/ml or less.

In an aspect of this invention, the material has an aqueous solubility of about 2 mg/ml or less.

In an aspect of this invention, the organic solvent has an aqueous solubility of about 25 mg/ml or less.

In an aspect of this invention, the organic solvent has an aqueous solubility of about 10 mg/ml or less.

In an aspect of this invention, the organic solvent has an aqueous solubility of about 2 mg/ml or less.

In an aspect of this invention, the addition of the organic solution to the aqueous solution is about 4 minutes to about 40 minutes in duration.

In an aspect of this invention, the addition of the organic solution to the aqueous solution is about 5 minutes to about 30 minutes in duration.

In an aspect of this invention, the addition of the organic solution to the aqueous solution is about 8 minutes to about 20 minutes in duration.

In an aspect of this invention, the concentration (mass/volume of solution) of material in the organic solution is about 0.5 gram/ml to about 10 ug/ml.

In an aspect of this invention, the concentration of material in the organic solution is about 0.2 gram/ml to about 100 ug/ml.

In an aspect of this invention, the concentration of material in the organic solution is about 0.1 gram/ml to about 10 mg/ml.

In an aspect of this invention, the concentration (mass/volume of solution) of emulsifier in the aqueous solution is about 20% to about 0.01%.

In an aspect of this invention, the concentration of emulsifier in the aqueous solution is about 10% to about 0.1%.

In an aspect of this invention, the concentration of emulsifier in the aqueous solution is about 5% to about 0.5%.

In an aspect of this invention, the material is an active agent.

In an aspect of this invention, the material is selected from the group consisting of halofuginone, ruboxistaurin, sirolimus, everolimus, zotarolimus, temsirolimus, pimecrolimus, biolimus, and any combination thereof.

In an aspect of this invention, the method further including after the completion of the addition of the organic solution, sonicating the aqueous solution to which the organic solution has been added for about 30 seconds to about 5 minutes.

In an aspect of this invention, the material dissolved in the organic solution is zotarolimus.

In an aspect of this invention, the organic solution is added over about 10 minutes.

In an aspect of this invention, the emulsifier is poly(vinyl alcohol).

In an aspect of this invention, the ratio of organic solution to aqueous solution is 1:20.

In an aspect of this invention, the sonication apparatus comprises a sonicator probe with a probe tip of about 6 mm.

In an aspect of this invention, the apparatus used for the addition of the organic solution to the aqueous solution comprises an 18-gauge needle.

In an aspect of this invention, the needle tip is about 1 mm lateral distance from the sonicator probe tip and about 1-2 mm vertical distance from the sonicator probe tip, and the sonicator probe tip is below the aqueous solution air interface.

DETAILED DESCRIPTION

DISCUSSION

Figure 1:
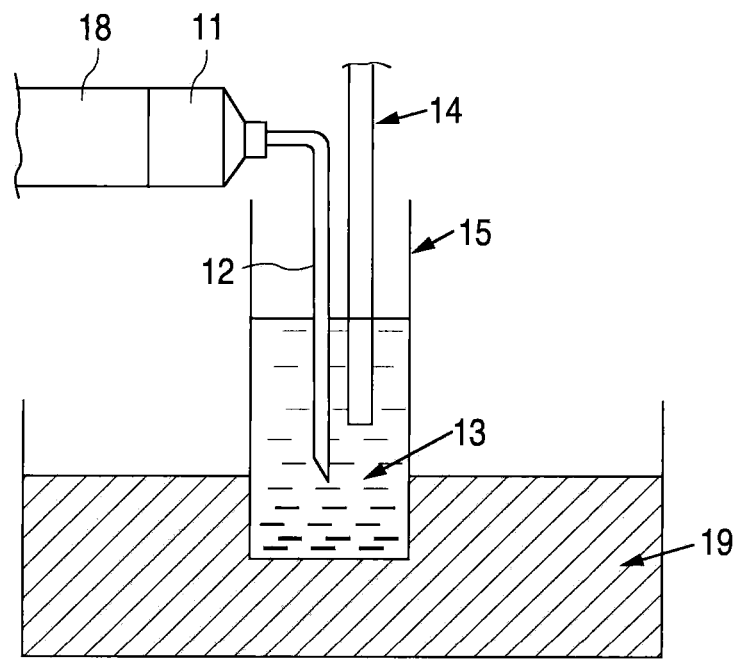
FIG. 1 depicts an exemplary experimental set-up.

Use of the singular herein includes the plural and visa versa unless expressly stated to be otherwise or obvious from the context that such is not intended. That is, "a" and "the" refer to one or more of whatever the word modifies. For example, "an active agent" may refer to one active agent, two active agents, etc. Likewise "the active agents" may mean one active agent or a plurality of active agents.

As used herein, unless specified otherwise, any words of approximation such as without limitation, "about," "essentially," "substantially" and the like mean that the element so modified need not be exactly what is described but can vary from the description by as much as ±15% without exceeding the scope of this invention.

As used herein, any ranges presented are inclusive of the end-points. For example, the statement "a temperature between 10° C. and 30° C." or "a temperature from 10° C. to 30° C." includes 10° C. and 30° C., as well as any temperature in between.

As used herein, an expression presented such as "not more than A, B, or C" or "at least X, Y, or Z" is equivalent in meaning to "not more than A, not more than B, or not more than C" or "at least X, at least Y, or at least Z," etc.

As used herein, "ultrasonic" refers to cyclic sound pressure at a frequency higher than that discernable by humans, typically 20,000 Hz and higher. "Ultrasonication" or sonication is the application of ultrasound pressure to a target.

As used herein, a "material" refers to a substance that is a solid at standard temperature and pressure, i.e., 20° C. and one atmosphere, and is capable of being dissolved in an organic solvent. The substance may be one or more elements, and/or one or more chemical compounds. Examples include active agents, organic compounds, polymers, oligomers and the like.

As used herein, an "active agent" refers to a substance that, when administered in a therapeutically effective amount to a patient suffering from a disease or condition, has a therapeutic beneficial effect on the health and well-being of the patient. A therapeutic beneficial effect on the health and well-being of a patient includes, but it not limited to: (1) curing the disease or condition; (2) slowing the progress of the disease or condition; (3) causing the disease or condition to retrogress; or, (4) alleviating one or more symptoms of the disease or condition.

As used herein, an active agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of an patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, an "active agent" also refers to pharmaceutically acceptable derivatives of the active agents specifically mentioned herein, including, but not limited to, salts, esters, amides, prodrugs, and the like.

As used herein, an "organic solvent" is a fluid the chemical composition of which includes carbon atom(s). The fluid may be liquid, gaseous or in a supercritical state. An organic solvent herein may be a blend of two or more such fluids.

As used herein, an "emulsifier" is a surface active agent which stabilizes an emulsion.

As used herein, "aqueous solubility," refers to the quantity of a material that can be dissolved in a given quantity of water, e.g. grams/100 grams or grams/100 ml, at a given temperature. If no temperature is given, it is assumed to be 25° C.

As used herein, "nano-particle" refers to a particle with an average diameter from about 1 nm to about 1000 nm.

As used herein, unless expressly stated otherwise, "average diameter" refers to the diameter as determined by dynamic light scattering (DLS), also referred to as photo correlation spectroscopy. Dynamic light scattering determines the hydrodynamic diameter or the Stokes diameter based on diffusion measurements, and includes solvent associated with the particle. For non-spherical particles, the reported "diameter" is actually the effective diameter, that is the diameter of a sphere with the equivalent hydrodynamic radius. This mean hydrodynamic diameter obtained from DLS is close to the volume-average diameter. A non-limiting example of a method for determining average diameters is International Standards Organization (ISO) 13321.

Particles are generally polydisperse, i.e., not all the same size. One measure of polydispersity is the ratio D90/D10. D90 and D10 are the diameters below which 90% and 10% of the particles fall for a number average diameter, or 90% or 10% of the surface area of the particles falls for the surface area average diameter, and the like. For the purposes of this invention D90 and D10 are determined by dynamic light scattering, discussed above, unless expressly stated otherwise.

The various aspects of the present invention are directed to methods for forming nanoparticles of a material having a narrow polydispersity.

A well-known general method for the preparation of particles is emulsion solvent evaporation. The method involves dissolving a material in an organic solvent that is immiscible or at least minimally soluble in water. An emulsion of the material-containing organic solvent in water containing an emulsifier is created with energy input such as from an ultrasonicator or a homogenizer. The organic solvent is then evaporated from the emulsion at a pressure ranging from vacuum to atmospheric. During solvent evaporation, the emulsion is continuously stirred with more vigorous stirring generally leading to smaller particle sizes.

It has now surprisingly been found that the size of particles obtained using the solvent emulsion method with a sonicator probe as the source of emulsion-forming energy is highly dependent on the spatial relationship of the probe tip and the injection point of the organic solution containing the material.

Various embodiments of the present invention are methods that allow for the production of nanoparticles of a material with a relatively low polydispersity. Although other methods, such as precision particle fabrication, allow for narrower particle distributions (precision particle fabrication can produce particles with a ratio of the volume average diameter to the number average diameter from 1.002 to 1.015), these methods require specialized equipment. The various methods of the present invention are methods that can be scaled up readily, and allow for tuning of particle size by changing the process parameters. The particle size resulting from the methods of the present invention is not largely impacted by the size of the tube delivering the organic solution to the aqueous solution, in contrast to precision particle fabrication where the tube size may be a significant factor.

Figure 2:
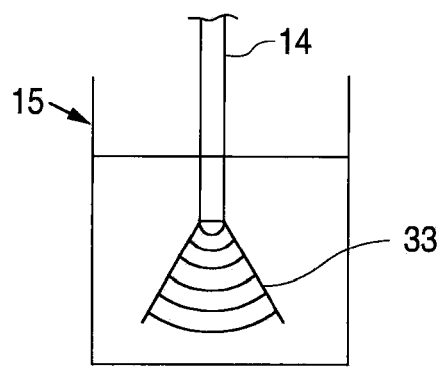
FIG. 2 depicts the sonication wave funnel observed for an exemplary experimental set-up.
Figure 3:
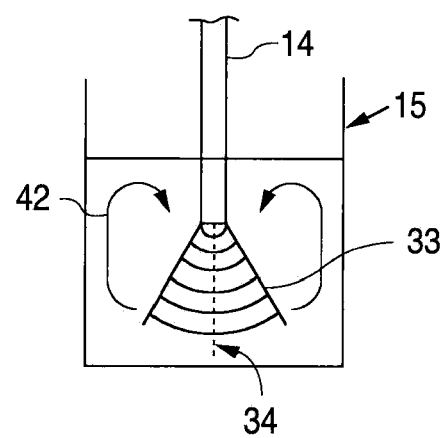
FIG. 3 depicts the flow pattern resulting from the sonication wave funnel observed for the exemplary experimental set-up depicted in FIG. 1.

An example of equipment that may be utilized is illustrated in FIG. 1. Organic solution 11 may be added via needle 12 to vial 15 containing aqueous solution with emulsifier 13 while undergoing sonication via sonication probe 14. The ultrasonic probe focuses the mechanical vibrations and power at the probe tip, resulting in a pressure wave, and cavitation, in the liquid. FIG. 2 illustrates an example of the funnel shaped pressure wave 33 ("sonication wave funnel") emanating from the tip of the sonicator probe 14. A pressure wave propagating from a point source will decrease in intensity (energy) with the square of the distance from the source if the wave propagates uniformly in all directions. For ultrasonication, wave intensity not only falls off with distance, but also due to the conversion of mechanical energy into heat. FIG. 3 illustrates the flow pattern as shown by arrows 42 in the vial 15 resulting from the sonication wave 33 from sonicator probe 14. The sonication wave funnel is visually observable. The waves are reflected off the bottom of the vial, and fluid flows in a circular pattern in the vial (or vessel).

Without being bound by theory, it is believed that the formation of nanoparticles with a reasonably narrow polydispersity results when the point of addition of the organic to the aqueous solution ("point of addition") is within the sonication wave funnel, and within a selected distance from the sonicator probe tip, the source of the sonication waves (wave source), where the selected distance depends upon the desired particle size.

With respect to the various methods of the present invention, the selected distance from the wave source depending on the desired particle size will depend upon a number of factors including, without limitation, the power delivered by the wave source and the size and shape of the wave source. As shown in FIG. 3, the wave emanates in an arc-like or hemispherical shape. The intensity (power) will be highest at the probe surface (wave source), and at centerline 34 (FIG. 3). The selected distance for producing nanoparticles of a desired size will be further from the wave source with a higher power input to the sonicator probe. If the point of addition is outside the sonication wave funnel, larger particles with a higher polydispersity result.

Figure 4:
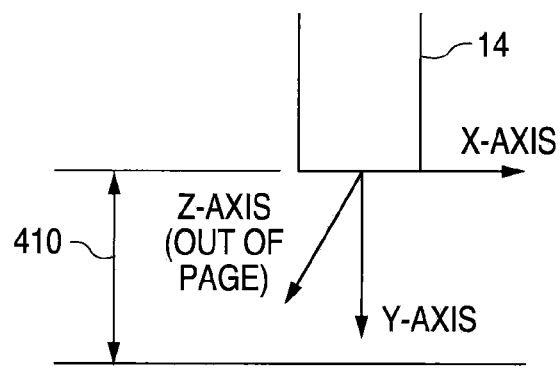
FIG. 4 depicts a close-up of the sonicator probe.
Figure 5:
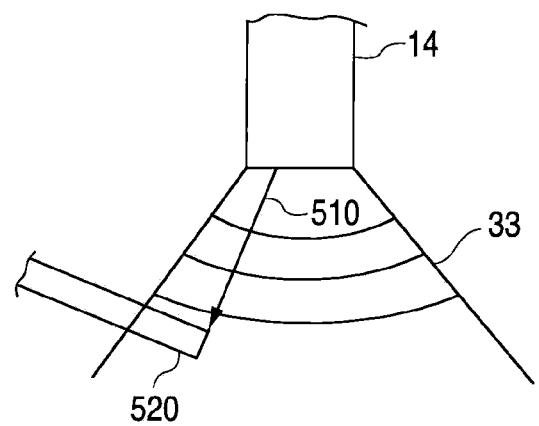
FIG. 5 depicts the wave fronts in an exemplary sonication wave.

In general, the selected distance from the wave source can be measured along an axis labeled y as shown in FIG. 4. In the various embodiments of the present invention, the point of addition will be, if nano-scale particles are desired, within the sonication wave funnel and at a selected distance measured perpendicular to the surface of the wave source that is distance 410 from point of addition X measured along the y-axis as shown in FIG. 4. Alternatively, the selected distance may be measured radially where radial distance is the distance between the point of addition 520 and the wave source 14 as measured by a radial line 510 emanating from the wave source and in the direction of wave propagation as depicted in FIG. 5. The selected distance, whether measured along a radial or the y-axis, may be not more than 300%, 200%, 100%, 80%, 60%, 40%, or 20% of the probe diameter. For purposes of this invention, for non-circular probes, the probe diameter will be the shorter dimension of the probe tip.

The wave intensity describes the transfer of energy per unit time through an area normal to the direction of wave propagation, and can be described as the power (W=J/s) per unit area. Wave intensity drops off with wave propagation. Thus, in some embodiments the selected distance is such that the wave intensity is not less than 70%, preferably not less than 80%, and most preferably at present not less than 90% of the initial wave intensity (power input to the sonicator probe divided by sonicator probe tip area).

Figure 6:
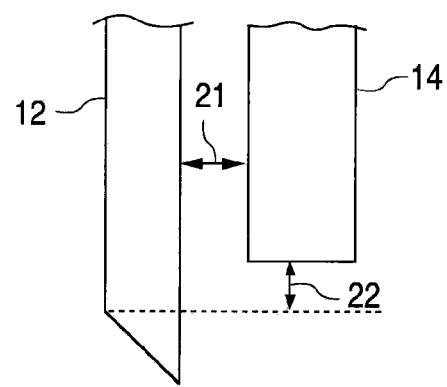
FIG. 6 depicts a close-up of the needle and probe of the exemplary experimental set-up depicted in FIG. 1.

A non-limiting example of the selected distance is illustrated in FIG. 6. A close-up of the needle and probe is depicted in FIG. 6 where the sonicator probe and needle are both inserted vertically into a vial, similar to that shown in FIG. 1. The vertical distance 22 is measured between the highest point for the point of addition and the level of the wave source and is about 1-2 mm. The lateral distance 21 in FIG. 6 is measured between the needle and the sonicator probe and is about 1 mm. These distances place the point of addition within the sonication wave funnel and a selected distance from the wave source allowing for the production of particles of a desired particle size. One of skill in the art will be able to determine the selected distance for obtaining various size particles using different strength ultrasonic wave generators and different probes based upon the disclosure herein without undue experimentation.

It is not necessary that the sonicator probe be placed into the vessel vertically. It may be placed into the vessel at any angle provided that excessive foaming at the surface does not occur. The wave source or probe may be located at the side or the bottom of a vessel provided that it does not touch the vessel. The probe may be located off-center. In a presently preferred embodiment, the probe is placed in the approximate center of the vessel so that a recirculation pattern, such as that depicted in FIG. 3, is obtained. The sonicator probe may be located at various depths within the vessel provided that the probe is at least in contact with the surface of the liquid. That is, the probe tip may be located a distance from the top of the fluid of about ¼, about ⅓, or about ½ of the total fluid height.

There may be multiple wave sources such as multiple transducers, and/or multiple sonicator probes, and there may also be multiple points of addition of organic solution. In some embodiments, there is one point of addition per wave source. In some embodiments, there may be fewer points of addition than wave sources, or vice-versa. There may be multiple points of addition within one sonication wave funnel.

Embodiments of the present invention encompass the use of various types of sonicators or sonication transducers. There is no specific power requirement for the sonicator or transducer used provided that it is capable of operating at a frequency of 20,000 Hz and higher. If a sonicator probe is used, any type of immersible probe capable of producing the appropriate sonication intensity may be used. The probe may be cylindrically shaped or it may taper in a gradual or stepwise manner to a smaller tip. A non-limiting example of a laboratory scale sonicator and probe is the Sonics VIBRA-CELL™ VCX 130, Model CV 18. This sonicator has a net power output of 130 Watts and can operate at 20,000 Hz. The standard probe is a titanium alloy of ¼" or 6 mm in diameter. Other sonicators or apparatus capable of producing a sonication wave may be used.

The methods are not limited to the shape and size of vessel illustrated in the figures. The vessel may be any other shape, and of a size to accommodate the probe, if a probe is to be used, and the apparatus used for the addition of the organic solution. The vessel may be sized to accommodate both the initial aqueous solution and the total final volume of the emulsion.

The flow rate of the organic solution and the concentration of the material in the organic solution are important parameters in controlling the size of the particles. If the flow rate is too high, larger particles may result as there is more organic material to be mixed with the aqueous material, and the mixing may be insufficient to produce a small emulsion droplet size. Without being bound by theory, it is believed that the slow addition of organic solution in the sonication wave at a point with high intensity results in the formation of small emulsion particles. It is believed that small emulsion particles result in the formation of small particles of material after the organic solvent has evaporated.

The flow rate is related to the duration of the addition of the organic solution to the aqueous solution ("addition duration"), and the ratio of the organic solution to aqueous solution. In some embodiments of the present invention, the ratio of organic solution to aqueous solution is about 1:5 to about 1:150, preferably about 1:10 to about 1:50, most preferably at present, not less than 1:12. For multiple points of addition, it is preferable that the addition duration is the same at all points of addition. In some embodiments, the addition duration is selected such that about 2.5% to about 25% of the total volume of the organic solution is added per minute, preferably about 3.3% to about 20% organic solution/minute, or presently most preferred about 5% to about 15% organic solution/minute. If there are multiple points of addition, the flow rates may be distributed among the multiple points of addition.

Any type of apparatus capable of controlling the rate of addition and the point of addition in the vessel may be used to add the organic solution to the aqueous solution. Any apparatus for dispensing the solution at a controlled rate (by volume or mass) over time may be used. Non-limiting examples include syringe pumps and other types of positive displacement pumps, centrifugal pumps, and peristaltic pumps. For multiple points of addition, a manifold may be used.

It is sometimes necessary to control the temperature of the aqueous solution during the sonication process as sonication results in heat generation. The vessel may be placed in an ice water bath, cooling coils may be placed in the vessel, or a cooling jacket may be placed around the vessel. The key is to maintain the temperature of the emulsion-forming solution at a temperature that is well below the melting point of the material of which nanoscale particles are to be formed.

The emulsion resulting from the addition of the organic solution to the aqueous solution may undergo additional processing operations. The emulsion may be sonicated for additional time such as, without limitation, for a duration of 5% to 35% of the initial organic solution addition time. Subsequently, the emulsion may be diluted with water in a range of 1:3 to 1:25, or presently preferred, in the range of 1:5 to 1:10. The diluted emulsion may be stirred under atmospheric pressure or under a vacuum for about 1 to 36 hours, allowing the solvent to evaporate, or to substantially evaporate. The emulsion may be centrifuged, the supernatant removed, and the resulting particles resuspended in an aqueous solution for particle size determination. The particles may be obtained by freeze-drying from the re-suspended dispersion.

The choice of materials, emulsifier and, particularly, the organic solvent, impacts particle size and polydispersity. Without being bound by theory, it is believed that some solvent evaporation occurs in the initial mixing and emulsification. Solvent evaporation may result from a local temperature rise and is aided by the high intensity mixing. Even with some method of temperature control, there may be some local heating, particularly close to the wave source. It is believed that the partial solvent evaporation occurring in the initial emulsification results in the emulsifier surrounding the emulsion droplets such that the particles are rapidly formed and subsequent agglomeration is limited. Limited aggregation of particles is, of course, related to relatively low polydispersity. Thus, some local temperature rise may be desirable. The lower the boiling point of the organic solvent the more pronounced the effect of localized temperature rise will be on the formation of nanoparticles as set forth herein. The methods of the present invention differ from other methods that rely upon partial miscibility of the organic solvent with water as the methods of the present invention use organic solvents of low aqueous solubility. Those skilled in the art will be able to select an organic solvent of appropriate boiling point based on the disclosures herein.

Examples of useful organic solvents include, but are not limited to, Dicholoromethane, Chloroform, and Ethyl acetate.

The concentration of the material in the organic solution impacts the final particle size with a higher concentration of material in organic solution yielding particles with a larger average diameter. The aqueous solubility of the organic solvent and the aqueous solubility of the material may also impact the particle size.

The emulsifier used in the process has an ability to partition to the organic solution/aqueous solution interface, and also may be subsequently washed away. Exemplary emulsifying agents include, but are not limited to, polyvinyl alcohol, polyvinyl pyrrolidone, sodium lauryl sulfate, sodium cholate, TWEEN 80™ (sorbitan monooleate polyethenoxy ether), diacetyl tartaric acid ester of mono- and di-glycerides, glycerol monostearate, glycerol monooleate, glycerol behenate, lecitihin, monosodium phosphate derivatives of mono and di-glycerides, phosphatidylcholine, stearylamine, and eoxycholic acid. A presently preferred emulsifier is 80% hydrolysed polyvinyl alcohol, Aldrich Cat # 360627-500G.

The aqueous solution preferably constitutes deionized water prepared by standard procedures well-known to those of ordinary skill in the art. No special purification of the water other than this is required although the purer the water the more reproducible the results of the process.

The particles resulting from the above process are nanoscale with a relatively narrow polydispersity. In some embodiments, the average diameter of the particles produced by the method is not more than 1 micrometer, 500 nanometers, 100 nanometers, or 12 nanometers. In a presently preferred embodiment the average diameter is not more than 500 nanometers. In some embodiments, the polydispersity of the particles produced by the method, represented by the ratio of D90/D10, is not more than 4, 3, 2, or 1.5. In a presently preferred embodiment, D90/D10 is not more than 2.

The resulting particles are substantially free of the organic solvent, and substantially free of the emulsifier. In some embodiments, the particles are less than 5% by weight solvent, preferable less than 2.5%, or presently more preferable less than 1%. The particles resulting from the process are substantially composed of the initial material dissolved in the organic solution. Put another way, the total content assay of the nanoparticles, which is a measure of the grams of material per grams of substance tested is not less than 85%, preferably not less that 90% and most preferably at present not less than 95% by weight of the initial material dissolved in the organic solution.

The material added to the organic solution may be an active agent. Examples of active agents that may be used in the method of this invention include, without limitation, anti-restenosis, pro- or anti-proliferative, anti-inflammatory, antineoplastic, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective active agents.

Examples of antiproliferative active agents include, without limitation, actinomycins, taxol, docetaxel, paclitaxel, sirolimus (rapamycin), biolimus A9 (Biosensors International, Singapore), deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin, 40-O-[2-(2-hydroxy)ethoxy]ethyl-rapamycin, 40-O-tetrazole-rapamycin, 40-O-tetrazolylrapamycin, 40-epi-(N1-tetrazole)-rapamycin, and pirfenidone.

Examples of anti-inflammatory active agents include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin active agents include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGI-OMAX® (bivalirudin, from Biogen), calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of cytostatic or antiproliferative active agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of ACE inhibitors include, without limitation, quinapril, perindopril, ramipril, captopril, benazepril, trandolapril, fosinopril, lisinopril, moexipril and enalapril.

Examples of angiogensin II receptor antagonists include, without limitation, irbesartan and losartan.

Any material or active agent of acceptable aqueous solubility as set forth herein may be used in the various embodiments of the present invention.

Presently preferred active agents are halofuginone, ruboxistaurin, sirolimus, everolimus, zotarolimus, temsirolimus, pimecrolimus and biolimus.

EXAMPLES

The following example is provided to aid in understanding the invention, but it is to be understood that the invention is not limited to the particular materials or procedures described.

Example 1

Nano-size particles of zotarolimus were manufactured with the apparatus shown in FIG. 1. The equipment included a 3 ml syringe 18 used with a syringe pump (not shown) and an 18 Gauge stainless steel needle 12, a sonicator, Sonics Vibracell, CV18 with the standard 6 mm probe 14, and a 40 mL glass vial 15 (height 95 mm×diameter 25 mm). The vial 15 was placed in an ice water bath 19. The equipment was set-up as shown in FIGS. 1 and 6 with the needle and sonicator probe placed vertically in the vial. The needle 12 and sonicator probe 14 are parallel to each other and separated by 1 mm. The highest point in the opening in the tip of the needle is 1-2 mm below the sonicator probe surface (see FIG. 6). The sonicator probe tip inserted into the solution to a point about ⅓ of the total height from the fluid surface.

An aqueous solution of 2.5% by weight of poly(vinyl alcohol) ("PVA"), 80% hydrolysed (Aldrich Cat# 360627-500G, Batch# 03630EH, MW: 9,000-10,000) was made, as well as a solution of 100 mg/ml zotarolimus in dichloromethane (Sigma Cat# 270997-2L). Twenty ml of the PVA solution was placed into the 40 ml glass vial, which was placed in a bath of ice and water. The sonicator probe was cleaned with acetone before use. The sonicator was used at 100% amplitude while dispensing the organic solution at 0.1 ml/min over 10 minutes. Care was taken to insure that the sonicator probe and the needle did not touch during the addition of the organic solution. The emulsion was then sonicated for an additional 2 minutes after the addition of the 1 ml of organic solution. The resulting emulsion was diluted by addition to 150 ml of deionized water. The diluted emulsion was stirred in the fume hood for 10 minutes and the particle size was measured with dynamic light scattering. Foam was removed from the surface before and during the stirring step.

The solution was stirred for an additional 12-24 hours under the fume hood to remove residual solvent. The particle size was measured again with dynamic light scattering. The particles were subsequently washed 3 times by the following process: the emulsion was centrifuged at 15,000 rpm for 20 minutes; after centriguation, the supernatant was decanted; the pellets in the bottom of the centrifuge tube were resuspended in deionzed water and sonicated in a sonicator bath. After the third washing process was complete, the particles were re-suspended in deionzed water, placed in a test tube, and then frozen with liquid nitrogen. The resulting nanoparticles were freeze-dried until completely dried which took about two days or more.

The size and polydispersity of the nanoparticles was determined by dynamic light scattering using a Brookhaven Instruments Corporation, 90 Plus Particle size analyzer with following settings: temperature: 25 C.; Viscosity: 0.98 cP; Refractive Index: 1.330; Light angle: 90.00; Wavelength: 658, and Refractive index of particles: 1.590. The instrument was validated with reference samples of polystyrene of 100 nm, 400 nm, 800 nm and 1 um in size manufactured by PolySciences Inc. The analysis software provided an average effective hydrodynamic diameter of 277.6 nm and a measure of polydispersity, the second moment of the distribution to the square of the first moment of the distribution, of 0.091.

While particular embodiments of the present invention have been shown and described, it will be obvious to those skilled in the art that changes and modifications can be made without departing from this invention in its broader aspects. The scope of the invention includes any combination of the elements or aspects of the invention from the different species or embodiments disclosed herein. Therefore, the claims are to encompass within their scope all such changes and modifications as fall within the true spirit and scope of this invention.

What is claimed:

1. A method for forming particles of a material comprising:
    adding an organic solution comprising a material and an organic solvent to an aqueous solution comprising an emulsifier and water in about 3 minutes to about 60 minutes wherein the ratio (volume:volume) of organic solution to aqueous solution is about 1:3 to about 1:500; and
    sonicating the aqueous solution during the addition of the organic solution;
    wherein the material has an aqueous solubility of 50 mg/ml or less, and the organic solvent has an aqueous solubility of 50 mg/ml or less;
    wherein the sonication apparatus is at least partially submersed in the aqueous solution but does not touch any part of the apparatus used in the addition of the organic solution to the aqueous solution; and
    wherein the point of addition of the organic solution to the aqueous solution is within the wave funnel produced by the sonication and within a selected distance from the wave source depending on the desired particle size.

2. The method of claim 1, wherein the sonication apparatus comprises a sonicator probe, having a diameter, that is at least partially submersed in the aqueous solution.

3. The method of claim 2, wherein the selected distance is not more than three times the probe diameter.

4. The method of claim 2, wherein the selected distance is not more than two times the probe diameter.

5. The method of claim 2, wherein the selected distance is not more than one probe diameter.

6. The method of claim 1, wherein the material has an aqueous solubility of about 10 mg/ml or less.

7. The method of claim 1, wherein the material has an aqueous solubility of about 2 mg/ml or less.

8. The method of claim 1, wherein the organic solvent has an aqueous solubility of about 10 mg/ml or less.

9. The method of claim 1, wherein the organic solvent has an aqueous solubility of about 2 mg/ml or less.

10. The method of claim 1, wherein the ratio of organic solution to aqueous solution is about 1:5 to about 1:150.

11. The method of claim 1, wherein the ratio of organic solution to aqueous solution is about 1:10 to about 1:50.

12. The method of claim 1, wherein the addition duration is about 4 minutes to about 40 minutes.

13. The method of claim 1, wherein the addition duration is about 5 minutes up to about 30 minutes.

14. The method of claim 1, wherein the concentration (mass/volume of solution) of material in the organic solution is about 0.5 gram/ml to about 10 ug/ml.

15. The method of claim 1, wherein the concentration (mass/volume of solution) of material in the organic solution is about 0.1 gram/ml to about 10 mg/ml.

16. The method of claim 1, wherein the concentration of emulsifier in the aqueous solution is about 10% to about 0.1%.

17. The method of claim 1, wherein the concentration of emulsifier in the aqueous solution is about 5% to about 0.5%.

18. The method of claim 1, wherein polydispersity of the particles produced by the method as determined by the ratio of D90/D10 is not more than 4.

19. The method of claim 1, wherein the material is an active agent.

20. The method of claim 1, further comprising, after the completion of the addition of the organic solution, sonicating the aqueous solution to which the organic solution has been added for about 30 seconds to about 5 minutes.

21. The method of claim 1, wherein
    the material is zotarolimus;
    the organic solution is added over about 10 minutes;
    the emulsifier is poly(vinyl alcohol);
    the ratio of organic solution to aqueous solution is about 1:20;
    the sonication apparatus comprises a sonicator probe with a tip of about 6 mm in diameter;
    the apparatus used for the addition of the organic solution to the aqueous solution comprises a 18-gauge needle; and,
    the needle tip is about 1 mm lateral distance from the sonicator probe tip and about 1-2 mm vertical distance from the sonicator probe tip.

* * * * *